(12) United States Patent
Lubon et al.

(10) Patent No.: US 6,518,482 B2
(45) Date of Patent: Feb. 11, 2003

(54) TRANSGENIC NON-HUMAN MAMMALS EXPRESSING HUMAN COAGULATION FACTOR VIII AND VON WILLEBRAND FACTOR

(75) Inventors: Henryk Lubon, Rockville, MD (US); William N. Drohan, Springfield, VA (US); William H. Velander, Blacksburg, VA (US)

(73) Assignees: American National Red Cross, Washington, DC (US); Virginia Tech Intellectual Properties, Inc., Blacksburg, VA (US)

(*) Notice: Subject to any disclaimer, the term of this patent is extended or adjusted under 35 U.S.C. 154(b) by 50 days.

(21) Appl. No.: 09/849,406

(22) Filed: May 7, 2001

(65) Prior Publication Data

US 2002/0062492 A1 May 23, 2002

Related U.S. Application Data

(62) Division of application No. 09/262,017, filed on Mar. 4, 1999, now Pat. No. 6,255,554, which is a division of application No. 08/308,518, filed on Sep. 21, 1994, now Pat. No. 5,880,327.

(51) Int. Cl.$^7$ ............................................. A01K 67/027
(52) U.S. Cl. ............................ 800/14; 800/7; 800/15; 800/16; 800/17; 800/18; 800/25; 435/325
(58) Field of Search ............................ 800/7, 14, 15, 800/16, 17, 18, 25; 435/325

(56) References Cited

U.S. PATENT DOCUMENTS

| | | | |
|---|---|---|---|
| 4,757,006 A | 7/1988 | Toole, Jr. et al. | 435/70 |
| 4,873,316 A | 10/1989 | Meade et al. | 530/412 |
| 5,288,846 A | 2/1994 | Quertermous et al. | 435/172.3 |
| 5,366,894 A | 11/1994 | Clark et al. | 435/320.1 |
| 5,880,327 A | 3/1999 | Lubon et al. | 800/14 |
| 6,255,554 B1 * | 7/2001 | Lubon et al. | 800/14 |

FOREIGN PATENT DOCUMENTS

| | | |
|---|---|---|
| WO | 88/00239 | 1/1988 |
| WO | 90/05188 | 5/1990 |
| WO | 91/08216 | 6/1991 |
| WO | 92/22644 | 12/1992 |

OTHER PUBLICATIONS

Cornelis L. Verweij et al., Full–length von Willebrand factor (vWF) cDNA encodes a highly repetitive protein considerably lager than the mature vWF subunit, The EMBO Journal vol. 5 No. 8 pp 1839–1986.*

David Bonthron et al., Nucleotide sequence of pre–pro–von Willebrand factor cDNA, Aug. 7, 1986, vol. 14, No. 17, 1986, Nucleic Acids Research.*

Kaufman, "Genetic Engineering of Factor VIII", Nature, 342:207–8, Nov. 1989.

Paleyanda et al., "The Expression of Therapeutic Proteins in Transgenic Animals", Recombinant Technology in Hemostasis and Thrombosis, 197–209, 1991.

Kaufman, "Expression and Structure–Function Properties of Recombinant Factor VII", Transfusion Medicine Reviews, 6; 4:235–46, Oct. 1992.

Mikkelsen et al., "Heterogeneity in the Tyrosine Sulfation of Chinese Hamster Ovary Cell Produced Recombinant FVIII", Biochemistry, 30:6;1533–37, 1991.

Hironaka et al., "Comparative Study of the Sugar Chains of Factor VII Purified from Human Plasma and from the Culture . . . ", The Journal of Biological Chemistry, 267:1–9, 1992.

Foster et al., "Factor VII Structure and Function", Blood Reviews, 3:180–91, 1989.

Wood et al., "Expression of Active Human Factor VII from Recombinant DNA Clones", Nature,–312:330–37, Nov. 1984.

R. Halter et al., Strategies to Express Factor VIII Gene Constructs in the Ovine Mammary Gland, Theriogenology 39:137–149, Jan. 1993.

R.J. Wall, "Transgenic Livestock: Progress and Prospects for the Future", Theriogenology 45:57–68, 1996.

Bondioli et al., "Production of Transgenic Cattle by Pronuclear Injection", Production of Transgenic Cattle, Chapter 22.

Roschlau et al., "Gene Transfer Experiements in Cattle", J. Reprod. Fert. Suppl., 38, 1989, pp. 153–160.

Krimpenfort et al., "Generation of transgenic dairy cattle using in vitro embryo production", Biotech., vol. 9, 9/91, pp. 844–847.

Houdebine, L.M. "Production of Pharmaceutical Proteins from Transgenic Animals", Journal of Biotechnology vol. 34, pp. 269–287, 1994.

Mullins et al., "Transgenesis in Nonmurine Species", Hypertension, vol. 22, No. 4, pp. 630–633, 1993.

* cited by examiner

*Primary Examiner*—Deborah Crouch
(74) *Attorney, Agent, or Firm*—Foley & Lardner

(57) ABSTRACT

A non-human transgenic mammalian animal, as described above, contains an exogenous double stranded DNA sequence stably integrated into the genome of the animal, which comprises cis-acting regulatory units operably linked to a DNA sequence encoding human Factor VIII protein and a signal peptide, where the cis-acting regulatory units are active in mammary gland cells and the signal peptide is active in directing newly expressed Factor VIII into the milk of the animal. The promoter may be a milk protein promoter such as for whey acidic protein, casein, lactalbumin, or beta-lactoglobulin promoter. The transgenic mammals are preferably farm animals, for example, cows, goats, sheep, rabbits and pigs. Concurrent expression of a gene for human von Willebrand's Factor into milk may be used to stabilize newly-secreted Factor VIII.

32 Claims, 3 Drawing Sheets

SEQUENCE LISTING

```
<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
ccccagctgc agccatgaag                                              20

<210> SEQ ID NO 2
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
ccccagggat atccctgcag ccatgaag                                     28
```

TRANSGENIC NON-HUMAN MAMMALS EXPRESSING HUMAN COAGULATION FACTOR VIII AND VON WILLEBRAND FACTOR

This Application is a Divisional of Application Ser. No. 09/262,017, filed Mar. 04, 1999, now U.S. Pat. No. 6,255, 554 B1, which is in turn a Divisional of Application Ser. No. 08/308,518, filed Sep. 21, 1994 now U.S. Pat. No. 5,880, 327.

BACKGROUND OF THE INVENTION

This invention relates generally to transgenic animals and their use as bioreactors for the production of clinically useful quantities of proteins. More specifically, this invention relates to a non-human transgenic animal genetically engineered to express recombinant human Factor VIII protein or von Willebrand Factor protein and to secrete newly expressed protein into a body fluid from which the protein can readily be isolated.

Factor VIII ("F8") is a blood plasma glycoprotein of about 260 kDa molecular mass produced in the liver of mammals. It is a critical component of the cascade of coagulation reactions that lead to blood clotting. Within this cascade is a step in which Factor IXa, in conjunction with F8, converts Factor X to an activated form, Factor Xa. F8 acts as a cofactor at this step, being required with calcium ions and phospholipid for the activity of Factor IXa. The two most common hemophilic disorders are caused by a deficiency of functional F8 (Hemophilia A, about 80% of all cases) or functional Factor IXa (Hemophilia B or Christmas Factor disease).

Until recently, the standard treatment of Hemophilia A involved frequent infusions of preparations of F8 concentrates derived from the plasmas of human donors. While this replacement therapy is generally effective, such treatment puts patients at risk for virus-transmissible diseases such as hepatitis and AIDS. Although this risk has been reduced by further purification of F8 from plasma by immunopurification using monoclonal antibodies, and by inactivating viruses by treatment with either an organic solvent or heat, such preparations have greatly increased the cost of treatment, and are not without risk. For these reasons, patients have been treated episodically, rather than prophylactically. A further complication is that about 15% of patients develop inhibitory antibodies to thus-prepared F8.

An important advance in the treatment of Hemophilia A has been the isolation of cDNA clones encoding the complete 2,351 amino acid sequence of human F8 (see, Wood et al, *Nature,* 312: 330 (1984) and U.S. Pat. No. 4,757,006, Jul. 12, 1988) and the provision of the human F8 gene DNA sequence and recombinant methods for its production).

Analysis of the deduced primary amino acid sequence of human F8 determined from the cloned cDNA indicates that it is a heterodimer processed from a larger precursor polypeptide. The heterodimer consists of a C-terminal light chain of about 80 kDa in a metal ion-dependent association with an about 210 kDa N-terminal heavy chain fragment. See review by Kaufman, *Transfusion Med. Revs.,* 6: 235 (1992). Physiological activation of the heterodimer occurs through proteolytic cleavage of the protein chains by thrombin (Factor IIa). Thrombin cleaves the heavy chain to a 90 kDa protein, and thence to 54 kDa and 44 kDa fragments. Thrombin also cleaves the 80 kDa light chain to a 72 kDa protein. It is the latter protein, and the two heavy chain fragments (54 kDa and 44 kDa above), held together by calcium ions, that constitute active F8. Inactivation occurs when the 72 kDa and 54 kDa proteins are further cleaved by thrombin, activated protein C or Factor Xa. In plasma, this F8 complex is stabilized by association with a 50-fold excess of von Willebrand Factor protein ("vWF"), which appears to inhibit proteolytic destruction of F8.

The amino acid sequence of F8 is organized into three structural domains: a triplicated A domain of 330 amino acids, a single B domain of 980 amino acids, and a duplicated C domain of 150 amino acids. The B domain has no homology to other proteins and provides 18 of the 25 potential asparagine(N)-linked glycosylation sites of this protein. Although porcine and human F8 show striking divergence in their B domains, the porcine protein can be used to treat Hemophilia A in humans. This suggests either that the B chain is not critical to the biological activity of the holomolecule, or that multiple versions of this domain are similarly effective. Porcine and human F8 show 80–85% homology in two of the three A domains.

Although the hepatocyte is likely to be the cell type that produces F8 in vivo, to date there are no known natural cell lines that express this protein. Kaufman, 1992, above, and Wood et al. 1984, above transfected transformed hamster kidney cells with a vector containing a gene that encodes F8, and expressed this protein. Kaufman, *Nature* 342: 207 (1989), expressed recombinant F8 in transformed CHO cells, but production and secretion of newly synthesized protein into the conditioned growth medium was very low. This was said to have been due to three factors: a requirement for the presence of the vWF in the conditioned medium used in these culture systems in order to protect newly secreted F8 from proteolytic destruction (in the absence of vWF, Factor VIII was secreted as incomplete chains that were subsequently degraded); incomplete secretion of newly synthesized F8 from the cells (most remained in the endoplasmic reticulum); and, a low level of F8 mRNA as a result of a post-translational event. Stable recombinant F8 was secreted by CHO cells only when the gene for vWF was concurrently expressed. Additional drawbacks to the use of mammalian tissue culture systems for the production of F8 in clinically useful quantities are the expense of growth media and the limited production capacity of mammalian tissue culture systems.

An important need remains for an efficient and relatively inexpensive means of producing large quantities of infectious particle-free, human F8 protein suitable for clinical use. The transgenic animal system described below that produces human F8 recombinantly satisfies this need.

It has been estimated, for example, by Paleyanda et al, in RECOMBINANT TECHNOLOGY IN HEMOSTASIS AND THROMBOSIS eds., Hoyer et al., (Plenum Press, NY 1991), that the U.S. market for F8 is about 600,000,000 units per year. At a specific activity of 5,000 U/mg, about 120 g a year are required. Assuming an achievable expression level of 50 mg/L in the milk of a transgenic animal of the invention and a 50% loss of the protein during purification, it has been estimated that about 1 cow (producing 6,000 L of milk yearly), 10 goats, sheep or pigs (producing 500 L of milk yearly), or 5,333 rabbits (producing 0.9 L of milk yearly) would be more than sufficient to supply all of this country's needs for F8 (Paleyanda et al., above).

SUMMARY OF THE INVENTION

It is therefore an object of this invention to provide a non-human, transgenic female mammalian animal that produces F8.

It is another object of the invention to provide a process for producing transgenic mammals with the aforementioned characteristic.

It is still another object of the invention to provide a method for producing F8 in commercially valuable amounts, by inducing a non-human transgenic female mammal to secrete expressed F8 into its milk, and isolating this protein from the milk.

It is yet another object to provide a transgenic animal that has had stably integrated into its genome DNAs encoding both F8 and vWF, such that both proteins are expressed and secreted into the animal's milk.

These objects have been realized by the production of a non-human transgenic female mammalian animal into whose genome is stably integrated an exogenous recombinant double stranded DNA sequence comprising a protein promoter specifically active in a secretory gland operably linked to a DNA sequence encoding F8 or vWF or both proteins and a signal peptide effective in directing secretion of newly expressed F8 protein into a body fluid of the animal. More particularly, the protein promoter is for a milk protein and the signal peptide directs the expressed F8 into the animal's milk.

These objects are also realized by the provision of double stranded DNA constructs comprising a tissue-specific active protein promoter operably linked to a DNA sequence encoding F8 or vWF and a DNA sequence encoding a signal peptide that directs newly expressed F8 or vWF into the host animal's body fluid, which constructs are used to produce the transgenic animal.

Other objects, features and advantages of the present invention will become apparent from the following detailed description and the appended claims. It should be understood, however, that the detailed description and examples given below, while indicating preferred embodiments, should not be considered limiting in any way as various changes and modifications within the spirit and scope of the invention will become apparent to the skilled artisan from this detailed description.

DETAILED DESCRIPTION OF THE INVENTION

Figure 1:
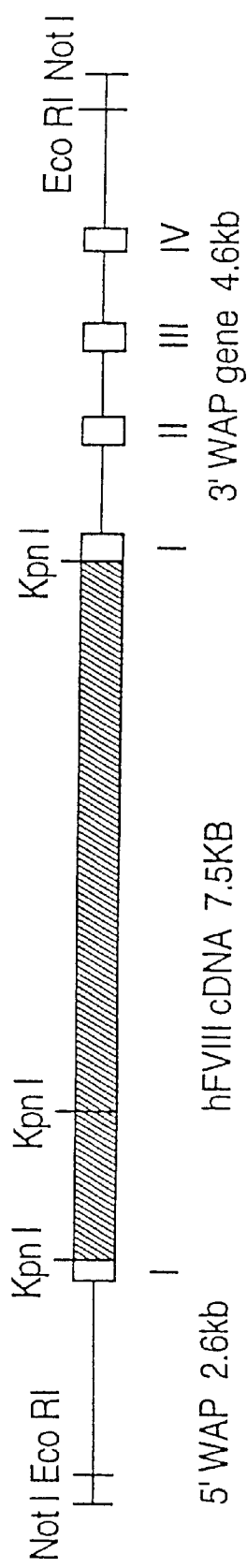
FIG. 1 is a schematic representation of a human F8 cDNA construct showing the contribution of whey acid protein ("WAP") genomic sequences. The 14.6 kb insert, composed of a 2.6 kb 5' WAP gene, a 7.5 kb human F8 cDNA and a 4.6 kb 3'WAP gene, can be excised by Not I digestion of the plasmid, releasing the 2.1 kb pPoly III D vector.

There has been invented a non-human transgenic female mammalian animal into whose genome is stably integrated an exogenous DNA sequence comprising a milk protein promoter specifically active in mammary gland cells operably linked to a DNA sequence encoding a human F8 protein and a signal sequence effective in directing secretion of newly expressed F8 protein into the milk of the transgenic animal.

The term "animal" here denotes all mammalian animals except humans. It also includes an individual animal in all stages of development, including embryonic and fetal stages. A "transgenic" animal is any animal containing cells that bear genetic information received, directly or indirectly, by deliberate genetic manipulation at the subcellular level, such as by microinjection or infection with recombinant virus.

"Transgenic" in the present context does not encompass classical crossbreeding or in vitro fertilization, but rather denotes animals in which one or more cells receive a recombinant DNA molecule. Although it is highly preferred that this molecule be integrated within the animal's chromosomes, the invention also encompasses the use of extrachromosomally replicating DNA sequences, such as might be engineered into yeast artificial chromosomes.

The term "germ cell line transgenic animal" refers to a transgenic animal in which the genetic information has been taken up and incorporated into a germ line cell, therefore conferring the ability to transfer the information to offspring. If such offspring, in fact, possess some or all of that information, then they, too, are transgenic animals.

The information to be introduced into the animal is preferably foreign to the species of animal to which the recipient belongs (i.e., "heterologous"), but the information may also be foreign only to the particular individual recipient, or genetic information already possessed by the recipient. In the last case, the introduced gene may be differently expressed than is the native gene.

The transgenic animals of this invention are other than human, and produce milk, blood serum, and urine. Farm animals (pigs, goats, sheep, cows, horses, rabbits and the like), rodents (such as mice), and domestic pets (for example, cats and dogs) are included in the scope of this invention.

It is highly preferred that a transgenic animal of the present invention be produced by introducing into single cell embryos appropriate polynucleotides that encode human F8 or vWF, or fragments or modified products thereof, in a manner such that these polynucleotides are stably integrated into the DNA of germ line cells of the mature animal, and are inherited in normal mendelian fashion.

Advances in technologies for embryo micromanipulation now permit introduction of heterologous DNA into fertilized mammalian ova. For instance, totipotent or pluripotent stem cells can be transformed by microinjection, calcium phosphate mediated precipitation, liposome fusion, retroviral infection or other means, the transformed cells are then introduced into the embryo, and the embryo then develops into a transgenic animal. In a highly preferred method, developing embryos are infected with a retrovirus containing the desired DNA, and transgenic animals produced from the infected embryo. In a most preferred method, however, the appropriate DNAs are coinjected into the pronucleus or cytoplasm of embryos, preferably at the single cell stage, and the embryos allowed to develop into mature transgenic animals. Those techniques as well known. See reviews of standard laboratory procedures for microinjection of heterologous DNAs into mammalian fertilized ova, including Hogan et al., MANIPULATING THE MOUSE EMBRYO, (Cold Spring Harbor Press 1986); Krimpenfort et al., *Bio/Technology* 9:88 (1991); Palmiter et al., *Cell*, 41: 343 (1985); Kraemer et al., GENETIC MANIPULATION OF THE EARLY MAMMALIAN EMBRYO, (Cold Spring Harbor Laboratory Press 1985); Hammer et al., *Nature*, 315: 680 (1985); Wagner et al., U.S. Pat. No. 5,175,385; Krimpenfort et al., U.S. Pat. No. 5,175,384, the respective contents of which are incorporated by reference.

Human F8 cDNA can be obtained by isolating it from an appropriate genomic source (i.e., human liver which is the natural organ for production of this protein) by alternate methods which include preparation of cDNAs from isolated mRNA templates, direct synthesis, or some combination thereof, as described by Wood et al. 1984 above, and Toole et al. U.S. Pat. No. 4,757,006, which are incorporated by reference.

The cDNAs encoding F8 or vWF or individual fragments or modified proteins thereof can be fused, in proper reading frame, with appropriate regulatory signals as described in detail below, to produce a genetic construct that is then amplified, for example, by preparation in a bacterial (e.g., *E. coli*) plasmid vector, according to conventional methods. See Sambrook et al., *Molecular Cloning: A Laboratory Manual* (Cold Spring Harbor Press 1989), the contents of which are incorporated by reference. The amplified construct is thereafter excised from the vector and purified for use in producing transgenic animals. Purification can be accomplished by means of one or more cycles of anionic HPLC; alternate techniques include ultracentrifugation through a sucrose or NaCl gradient, gel electrolution followed by agarose treatment and ethanol precipitation, or low pressure chromatography. Purification by several cycles of HPLC allows for remarkably high transformation frequencies, on the order of 20% or more in both mice and pigs.

Although the present invention preferably entails the use of DNA constructs that produce the desired or native human F8 protein or vWF per se, the desired protein also may be produced as a fusion protein containing another protein. For example, the desired recombinant protein of this invention may be produced as part of a larger recombinant protein in order to stabilize the desired protein or to make its purification from milk faster and easier. The fusion partners then are separated chemically or enzymatically, and the desired protein isolated.

Recombinant human F8 ("rhF8") may also be produced having the identical sequence as the native molecule, or it may be produced as a fragment or derivative. A variety of modified rhF8 or subunits thereof can be produced by altering a cloned DNA using the well-known techniques of in vitro mutagenesis such as those set out in the references above.

Production of transgenic animals containing the gene for rhF8 involves the use of cDNA or genomic DNA that encodes the precursor protein or heterodimeric rhF8. The full length base sequence of each protein chain is disclosed in the aforementioned publication of Wood et al. and Toole et al., above.

DNA constructs useful in the present invention provide a double stranded DNA sequence encoding rhF8 or rhvWF operably linked to all of the cis-acting signals necessary for mammary gland-specific expression of this protein, post-translational glycosylation and secretion of the protein into milk or other body fluids, and expression of full biological activity.

Modified F8 or vWF DNA sequences also can be employed in this invention. Useful modifications within this context include, but are not limited to, those that alter post-translational modifications, size or active site, or that fuse this protein or portions thereof to another protein. Such modifications can be introduced into the protein by techniques well known in this art, such as by synthesizing modified genes by ligation of overlapping oligonucleotide or introducing mutations into the cloned genes by, for example, oligonucleotide-mediated mutagenesis.

The cis-acting regulatory regions useful in the invention include the promoter that drives expression of the F8 or subunit chain genes. Highly preferred are promoters that are specifically active in mammary gland cells and that involve milk proteins. Among such promoters, highly preferred are the short and long WAP, short and long α, β and kappa casein, α-lactalbumin and β-lactoglobulin ("BLG") promoters.

Promoters may be selected on the basis of the protein compositions of various milks. For example, the WAP and BLG promoters are particularly useful with transgenic rodents, pigs and sheep. The rodent WAP short and long promoters have been used to express the rat WAP gene, the human tPA gene and the CD4 gene, while the sheep BLG promoter has been used to express the sheep BLG gene, the human alpha-1-antitrypsin gene and the human Factor IX gene. For reviews see Paleyanda et al., 1991, above, and Clark et al., *TIBTECH* 5: 20 (1987), the respective content of which are incorporated herein by reference. Preferred among the promoters for carrying out the present invention are the rodent casein and WAP promoters, and the casein, α-lactalbumin and BLG promoters from porcine, bovine, equine and ovine (pigs, sheep, goats, cows, horses), rabbits, rodents and domestic pets (dogs and cats). The genes for these promoters have been isolated and their characterizations published. For reviews see Clark et al. (1987), above, and Henninghausen, *Protein Expression and Purification*4 1: 3 (1990), the respective contents of which are incorporated herein by reference.

The promoter may be isolated by carrying out conventional restriction endonuclease and subcloning steps. A mouse WAP promoter, isolated as a 2.6 kb EcoR1-Kpn1 fragment immediately 5' to the WAP signal sequence, is preferred, although the "long" WAP promoter (the 5' 4.2 kb Sau 3A-Kpn1 promoter of the mouse WAP gene, or a fragment thereof) is also suitable for carrying out this invention.

Important to the present invention are regulatory sequences that direct secretion of proteins into milk and/or other body fluids of the transgenic animal. In this regard, both homologous and heterologous regulatory sequences are useful in the invention. Generally, regulatory sequences known to direct the secretion of milk proteins, such as either signal peptides from milk or the nascent target polypeptide, can be used, although signal sequences can also be used in accordance with this invention that direct the secretion of expressed proteins into other body fluids, particularly blood and urine. Most preferred for the transgenic mouse are the regulatory sequences for the WAP protein.

Among the useful sequences that regulate transcription, in addition to the promoters discussed above, are enhancers, splice signals, transcription termination signals, and polyadenylation sites. Particularly useful in this regard are those that increase the efficiency of the transcription of the genes for F8 or vWF in the mammary gland or other cells of the transgenic animals listed above. Preferred are transcription regulatory sequences for proteins highly expressed in the mammary gland cells (see above).

Preferably, the expression system or construct of this invention also includes a 3' untranslated region downstream of the DNA sequence encoding the desired recombinant protein, or the milk protein gene used for regulation. This region apparently stabilizes the RNA transcript of the expression system and thus increases the yield of the desired protein. Among the 3' untranslated regions useful in this regard are sequences that provide a poly A signal. Such sequences may be derived, e.g., from the SV 40 small t antigen, the casein 3' untranslated region, or other 3' untranslated sequences well known in this art. Preferably, the 3' untranslated region is derived from a milk-specific protein. The stabilizing effect of this region's poly A transcript is important in stabilizing the mRNA of the expression sequence. Also important in increasing the efficiency of expression of F8 are ribosome binding sites. Likewise, sequences that regulate the post-translational modification of F8 are useful in the invention.

Thus, in accordance with this invention, a double-stranded chimeric DNA including genes encoding the F8 or vWF proteins or both, operably linked to cis-acting regulatory sequences that promote efficient expression of the former in milk and/or other body fluids are introduced into an embryo where they are integrated into the embryonic genome and become part of the inheritable genetic endowment of all of the animals cells, including the germ line cells, of the adult that matures from the embryo. The recombinant proteins thus expressed and secreted into milk are immunologically reactive, as can be measured by an ELISA assay to be described below.

Where the synthesis of a F8 subunit chain may be limiting in the production of the holoprotein, expression of this chain an be increased by placing the gene in a different genomic locus. This other locus can contain a DNA sequence under the same or a different regulatory sequence than other sequences.

Figure 2:
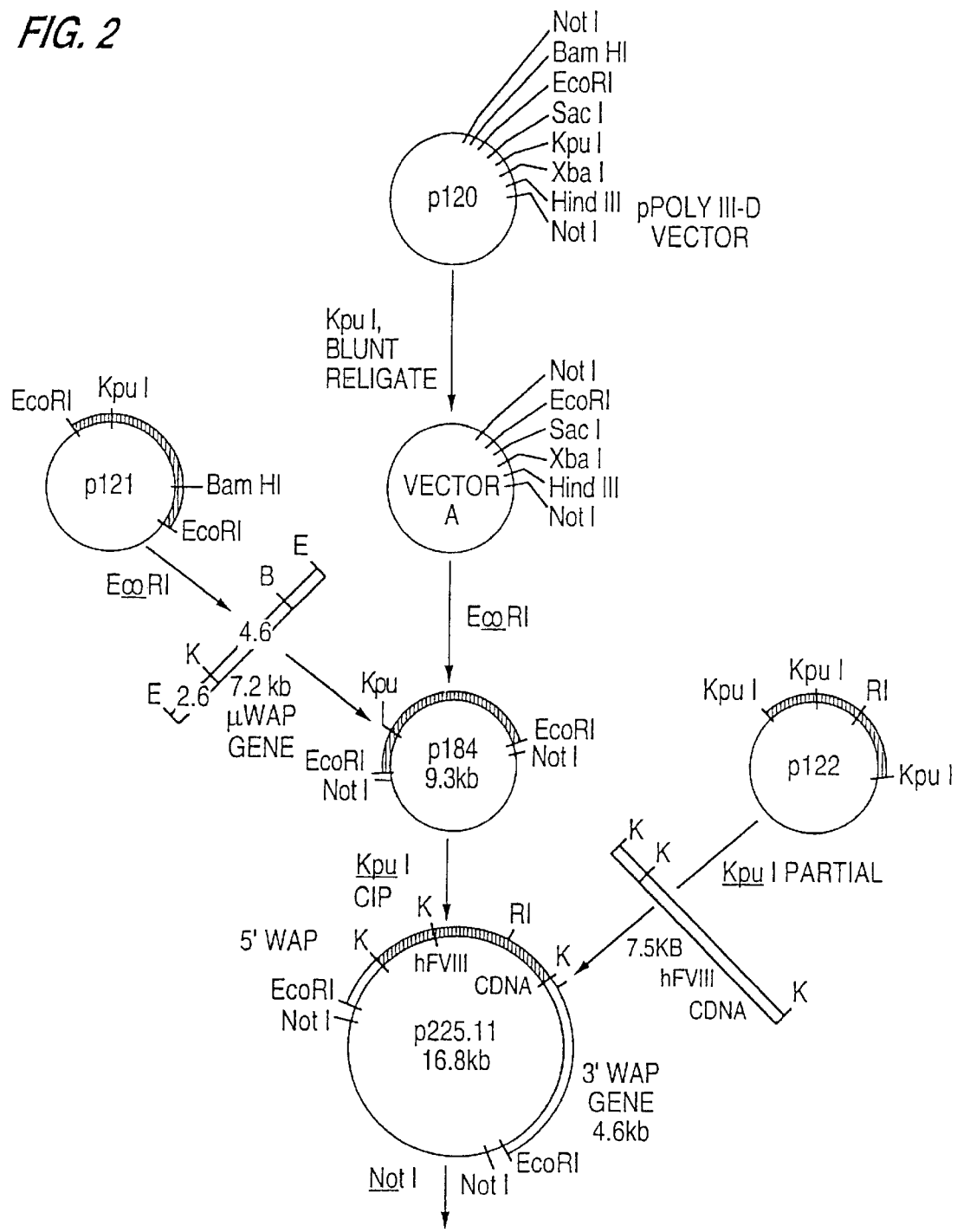
FIG. 2 is a schematic representation of the production of a mouse WAP-Human F8 cDNA hybrid gene, showing the insertion of a 7.5 kb human F8 cDNA at the Kpn I site of the mouse WAP gene, in the p225.11 plasmid.

In a particularly preferred embodiment, the transgenes of the invention generally consist of WAP milk protein upstream and downstream flanking the F8 cDNA/signal peptide sequences (FIGS. 1 and 2). A native 5'-WAP regulatory sequence ending in an accessible restriction site immediately before/at the ATG codon may be ligated to the restriction sites that occur at the ATG of translatable sequences with no linker sequences derived from the chains of human F8. Each of the combined 5'-regulatory and F8 translatable sequences ending in a particular restriction site may then be ligated to a corresponding restriction site which occurs at the beginning of the 3'-untranslated region of WAP and adjoining WAP 3'-flanking region. This construction motif enables native 5'-regulatory and 3'-UTR of the milk protein genes to be immediately juxtaposed without intervening sequences. Particular restriction sites at the ends of all constructs may be selected in order to facilitate concatenation of constructs into a single domain within the animal genome.

Although the above general descriptions of the DNA constructs of the invention have been given in terms of the WAP promoter, it is emphasized that other suitable promoters (see above for discussion) may be ligated to the fibrinogen encoding polynucleotides in a similar manner. By way of illustration, the following discussion describes the use of the BLG promoter to increase the efficiency of expression of F8 and F8-BLG fusion proteins in mammary glands.

By means of techniques described above, F8-encoding cDNA can be inserted into an ovine BLG gene. For instance, in order to produce such a construction, the 11.2 Kbp ovine BLG gene may be modified to possess a unique EcoRV site upstream of the initiator ATG codon in the vector pUCX-SRV. The sequence around this region is changed as follows:

```
                              PvuI       MetLys
Seq. ID No. 1 Natural  CCCCAGCTGCAGCCATGAAG EcoRV            MetLys
Seq. ID No. 2 pUCXSRV  CCCCAGGGATATCCCTGCAGCCATGAAG
```

This allows the cloning of blunt end fragments upstream of the BLG gene. The 7.5 kbp fragment from a plasmid (e.g., p122, FIG. 2) containing a CDNA encoding hF8 is isolated, blunt ends are generated with T4 DNA polymerase, and the product is ligated to EcoRV-cleaved pUCXSRV. Following transformation of E. coli with this plasmid, clones that are produced can be characterized by restriction analysis of plasmid DNA prepared by a mini-prep method and by determination of the nucleotide sequence around the 5' and 3' cloning junctions for the DNA. Clones having the desired structure can be used to produce transgenic rodents, pigs, sheep, cows, horses and other farm animals and domestic pets (cats and dogs) that secrete a F8-BLG fusion product into their biological fluids as described below.

A human F8 genomic sequence also may be fused to the ovine BLG promoter illustrated in the following discussion. DNA sequences encoding ovine BLG in plasmid pUCXSRV are deleted to generate a vector containing only ovine BLG promoter sequences (pUCSV). As with pUCSRV, blunt ended fragments may be fused to this promoter region by ligation to a unique EcoRV site. The sequences 5' to this site are identical in both plasmids.

Genomic F8 sequences of greater than about 15 kbp can be introduced into transgenic animals, despite their length, through the use of cosmids with overlapping F8 sequences, whereupon the necessary assembly of an entire genomic polynucleotide encoding hF8 is achieved by homologous recombination in vivo after microinjection into an embryo cell. In constructs useful in the foregoing example, a plasmid in which the F8 genomic sequences are fused to ovine BLG 3' flanking sequences just after the F8 translation termination codon to ensure proper transcription, termination and polyadenylation. The hF8 gene fused to ovine BLG 3' flanking sequences is excised from the plasmid, the 3' overhangs repaired using Klenow enzyme, and the product ligated to EcoRV-cleaved pUCSR. Following transformation of E. coli, the resulting clones are characterized by restriction DNA analysis and by determining the nucleotide sequences around the 5' and 3' cloning junctions. Clones having the desired structure may be introduced into fertilized animal ova for production of transgenic animals.

A variety of vectors based on the BLG gene may be constructed. In constructs based on this approach, the sequences encoding the ovine BLG protein are deleted, but the 5' promoter sequences are retained. Each may possess a different complement of introns from the ovine gene and a unique EcoRV site allowing the cloning of blunt ended fragments between the promoter and 3' flanking region of the gene. However, each contains the BLG promoter, the EcoRV site and the BLG 3'-flanking sequence. For each recombinant, the 7.5 kbp KpnI fragment from p122 is isolated, blunt ends generated as above, and the product ligated to EcoRV-cleaved vector sequences. Those constructs with the proper structures (determined as described above) may be used to express F8 in the biological fluids of transgenic animals.

Doubly-transgenic mice which have native BLG genomic sequences that are injected as separate constructs to be concatenated in vivo as additional flanking sequences to the BLG target cDNA construct (such as, BLG promoter-Intron I-EcoRV-Intron VI-BLG 3' flank plus BLG) give higher expression more frequently than that observed with the use of constructs of the BLG promoter-F8 cDNA-BLG gene or BLG promoter-F8 genomic (± BLG 3' end). Intact or native BLG genomic sequences that are preligated to the BLG-cDNA target may give the same advantage. This same principle can be extended to WAP genomic sequences.

Obtaining milk from a transgenic animal according to the present invention is accomplished by conventional means. See, e.g., McBurney et al., *J. Lab. Clin. Med.* 64: 485 (1964); Velander et al., *Proc Natl. Acad. Sci. USA* 89: 12003 (1992), the respective contents of which are incorporated by reference. F8 or vWF or fragments thereof or protein products thereof can be isolated and purified from milk or urine by conventional means without deleteriously affecting activity. A preferred method consists of a combination of anion exchange and immunochromatographies, cryoprecipitations, zinc ion-induced precipitation of either whole milk or milk whey (defatted milk) proteins. For these techniques, see Bringe et al., *J. Dairy Res.* 56: 543 (1989), the contents of which are incorporated herein by reference.

Milk is known to contain a number of proteases that have the potential to degrade foreign proteins. These include in the main an alkaline protease with tryptic and chymotryptic activities, a serine protease, a chymotrypsin-like enzyme, an aminopeptidase and an acid protease. Clark et al. (1987) above. It may be desirable therefore to protect newly secreted F8 or fragments thereof against proteolytic degradation. Such precautions include rapid processing of the milk after collection and addition to the milk of well known inhibitors of proteolysis, such as are listed in SIGMA CHEMICAL CO. CATALOG (1993 edition) at page 850, the contents of which are incorporated herein by reference.

As discussed above, under physiological conditions vWF complexes with circulating F8 and stabilizes the latter from degradation. In the present invention, the cDNA for vWF, which is available from the American Type Culture Collection, Rockville, Md. may be assembled into a construct similar to that described in FIGS. 1 and 2 and microinjected into an ambryo concurrently with the F8 construct. Under such conditions, both proteins will be expressed and secreted into the milk.

For determination of newly secreted F8 and/or vWf in milk whey, we have used the immunoradiometric ELISA assays essentially according to Hoyer et al., *Methods Enzymol.* 84: 51, 56–57 (1982), which is incorporated herein by reference. F8 antigens are measured with an radioiodinated human anti-F8 Fab' inhibitor antibody derived from patients with autoantibodies or transfused hemophiliac patients who have developed inhibitors. vWF antigens are measured with rabbit antibodies obtained by immunization with purified F8. Both assays use radiolabeled antibody that has been purified from immune complexes. Antigen measurement in these assays is based on the differential solubility of the antigen-antibody complexes and free antibody in ammonium sulfate solutions.

The following examples are provided merely to illustrate the invention, and are not to be interpreted as limiting the scope of the invention which is described in the specification and appended claims.

EXAMPLE 1

Construction of mWAP-hF8 CDNA Hybrid Gene

A pPoly III-D vector (p120 in FIG. 2) was restricted with Kpn 1, blunt ended and relegated to produce vector A without a Kpn 1 site.

A 7.2 kb mWAP gene was excised from the p121 plasmid with Eco R1, blunted, and ligated into Vector A that was linearized with Eco R1. The product was a 9.3 kb plasmid (labeled p184) in which the WAP gene was flanked by Eco R1 and adjacent Not 1 restriction sites.

Partial digestion of plasmid p122 with Kpn 1 produced a 7.5 kb F8 cDNA flanked by Kpn 1 restriction sites. This cDNA was then inserted into plasmid p184 at a Kpn 1 site within the mWAP gene to produce plasmid p225.11, a 16.8 kb plasmid. Flanking the human F8 gene is a 2.6 kb 5'mWAP segment with an upstream Not 1 site, and a 4.6 kb 3' mWAP gene with a downstream Not 1 site.

As shown in FIG. 1, the 14.7 kb insert comprising the 5' mWAP/hF8/3' mWAP hybrid gene can be excised by Not 1 digestion of the p225.11 plasmid, thereby releasing the 2.1 kb pPoly III-D vector.

The p225.11 plasmid has been deposited in the American Type Culture Collection, Rockville, Md. (ATCC Accession No. _____ ). Applicants hereby provide assurances that: (1) during the pendency of this patent application access to the deposited plasmids will be made available to persons properly designated by the Commissioner of Patents and Trademarks; (2) subsequent to the issuance of this patent, the plasmids will be made available to the public without restriction for the enforceable life of the patent, or for five years after the last request for a sample, or for thirty years, whichever is longest; and, (3) nonviable plasmids will be replaced.

EXAMPLE 2

Assay for Factor VIII Protein in Milk Whey by an ELISA Assay

The ELISA assay was used to estimate the concentration of hrF8 in the milk whey of transgenic mice produced with the mWAP promoter system described above by the following procedure.

Materials:
Whey, mouse f2.1.9.10
Whey, mouse f2.13.9
Whey, mouse f2.1.13.13
Whey, mouse f2.1.22.8
Whey, control mouse D15
Thrombin buffer: 0.15 M NaCl, 20 mM HEPES, 5 mM CaCl$_2$, 0.01% Tween 80, pH 7.4.
Thrombin: 2 U/ml
TBS: 20 mM Tris, 500 mM NaCl, pH 8.0
TBS/T: TBS with 0.05% Tween 20
TBS/T/NFDM: with 5% non-fat dry milk
Primary antibody in 1× TBS/T/NFDM:
  mAb 413 (2 µg/ml final; anti-heavy chain)
  mAb 37 (5 µg/ml final; anti-light chain)
Secondary antibody diluted 1:6000 in 1× TBS/T Streptavidin, alkaline phosphatase conjugate (GIBO)
LumiPhos Luminescent Biotin-conjugated development system (Boehringer-Mannheim)

Procedure:
1) Whey samples (200 µg total protein) were digested with thrombin (130 µU/µL) for 5 mins. After adding an equal volume of 2× Sample Buffer, samples were boiled for 5 mins, and quickly cooled in ice.
2) After running samples on a 1.2 mm thick 7.5% acrylamide Laemmli gel, proteins were electroblotted onto a nitrocellulose membrane at 12 v for 1.5 h. Membranes were stored in TBS as 4° C.

3) After blocking membranes in TBS/T/NFDM for 1 h and washing 3 times in TBS/T, the membrane was exposed to primary antibody for 2 h at room temperature, excess antibody was removed, and the membrane washed 3 times in TBS/T.
4) Membranes were exposed to secondary antibody for 15 mins. at room temperature, then washed 4 times with TBS/T.
5) After incubating membranes in LumiPhos according to the manufacturer's directions for 20 mins. in the dark, Kodak XAR-5 film was exposed to the membranes for 25 mins., and the film read in a densitometer.

The results of ELISA tests are shown in the table below.

| PDL Designation | Sample vol.* | Factor VIII antigen | |
| --- | --- | --- | --- |
| Mouse ID no. | µl | units/ml | ng/ml |
| Control D15 | 100 | 0.041 | 8.2 |
| F2.1.13.9 | 100 | 0.045 | 9.0 |
| F2.1.9.10 | 50 | 0.100 | 20.0 |

-continued

| PDL Designation | Sample vol.* | Factor VIII antigen | |
| --- | --- | --- | --- |
| Mouse ID no. | µl | units/ml | ng/ml |
| F2.1.22.8 | 40 | 0.144 | 28.8 |
| F2.1.13.13 | 50 | 0.093 | 18.6 |

*Samples stored at −20° C. In 2 animals, storage of the milk at 4° C. led to reduced ELISA values.

Relative to the background value for this method (control mouse D15), antigen (F8) production was elevated on an average of about 250% in three of four mice.

EXAMPLE 3

Western Blots of Mouse Whey Samples

Figure 3:
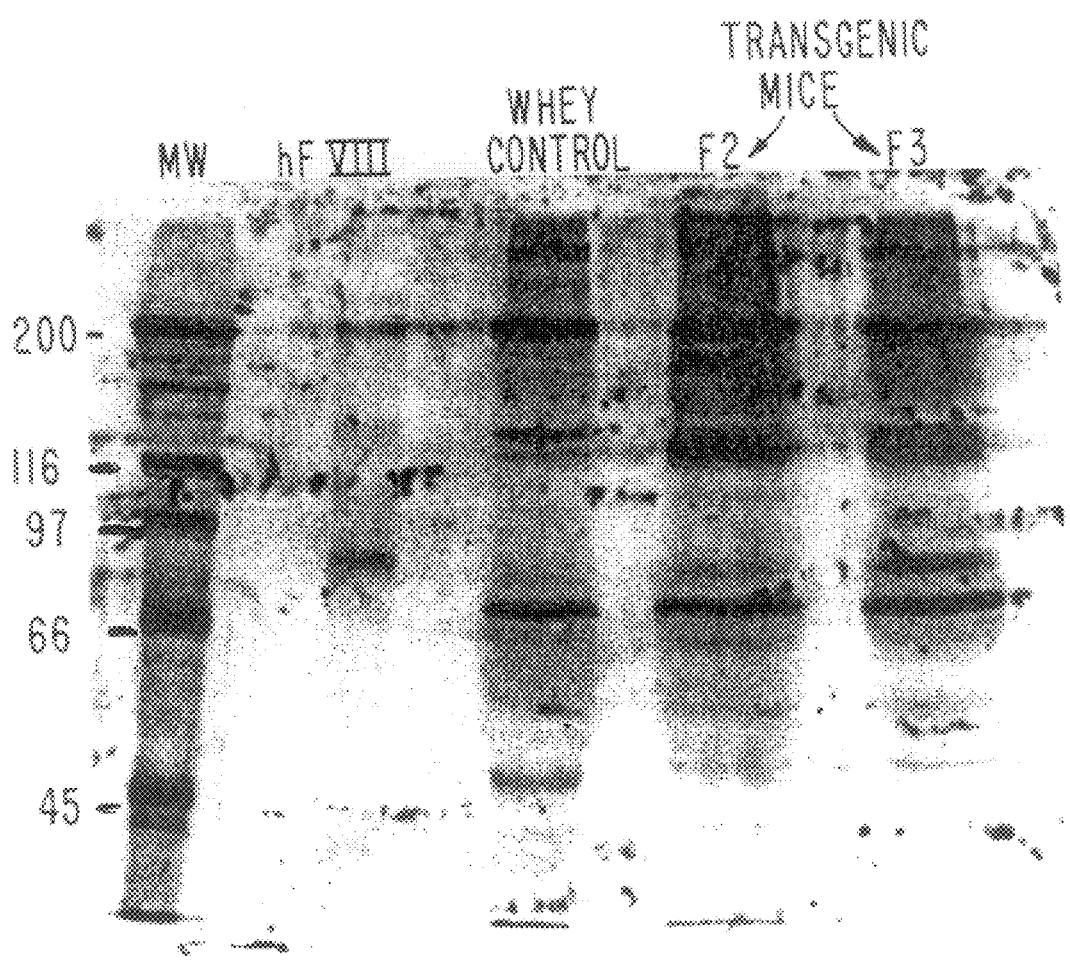
FIG. 3 is a sketch showing a Western blot of separated milk whey proteins obtained from transgenic mice induced to express human F8 into their milk. The first lane on the left shows molecular weight markers. The next lane shows authentic human F8 with major bands at about 80 kDa and about 210 kDa. The next lane shows the proteins in control whey. Lanes marked F2 and F3 show the proteins in the whey of transgenic mice induced to express recombinant human F8.

Milk wheys from two transgenic mice (F2 and F3) were immunoblotted in order to identify rhF8 in the samples. Western blots are shown in the sketch of FIG. 3.

The first lane on the left consists of molecular weight markers from 45 to 200 kDa. The second from the left lane is standard hF8 showing a major band at about 80 kDa and another at about 210 kDa. The third lane from the left shows control whey proteins. The F2 and F3 lanes show transgenic milk wheys; there were strongly staining new bands at about 80 kDa, compared to the control, in parallel to the standard hF8. The F2 and F3 lanes also show intensely staining bands at about 120 kDa, a band that is relatively faint in the control and apparently absent from standard hF8. Its identity is unknown.

Taken together, the data of Examples 2 and 3 demonstrate that the transgenic mice of the invention expressed authentic recombinant human F8 and secreted this protein into the animal's milk.

We claim:

1. A non-human transgenic mammal that produces in its mammary gland cells and secretes into its milk at detectable levels human von Willebrand Factor or fragment thereof which retains physiological activity of human von Willebrand Factor, wherein said transgenic mammal has stably integrated into its genome an exogenous gene construct comprising:

(A) 5' expression regulating sequences, including a mammary gland-specific promoter;

(B) DNA encoding said von Willebrand Factor or fragment thereof, and a signal sequence effective in directing secretion of said von Willebrand Factor or fragment thereof into the milk of said transgenic mammal; and (C) 3' regulatory sequences, including a polyadenylation signal, that result in the expression of said DNA encoding said von Willebrand Factor or fragment thereof, in said mammary gland cells, wherein (A), (B) and (C) are operably linked in said exogenous gene construct to obtain production of said von Willebrand Factor or fragment thereof in said mammary gland cells and secretion thereof into the milk of said transgenic mammal.

2. The non-human transgenic mammal according to claim 1, wherein said promoter is a milk protein gene promoter.

3. The non-human transgenic mammal according to claim 2, wherein said milk protein gene promoter is selected from the group consisting of whey acidic protein, casein, lactalbumin and beta-lactoglobulin promoters.

4. The non-human transgenic mammal according to claim 1, wherein said transgenic animal produces human von Willebrand Factor.

5. The non-human transgenic mammal according to claim 4, wherein said human von Willebrand Factor has the amino acid sequence of human von Willebrand Factor.

6. The non-human transgenic mammal according to claim 1, wherein said 3' regulatory sequences in said exogenous gene construct are 3' untranslated regions from a milk protein gene or from a human von Willebrand Factor gene.

7. The non-human transgenic mammal according to claim 1, wherein said transgenic mammal is selected from the group consisting of a mouse, rat, rabbit, pig, sheep, goat and cattle.

8. The non-human transgenic mammal according to claim 1, wherein said mammal is a female.

9. The non-human transgenic mammal according to claim 1, wherein said exogenous gene construct comprises a mouse whey acid protein promoter and the 3'regulatory sequence of the mouse whey acid protein gene.

10. A process for producing recombinant human von Willebrand Factor or fragment thereof which retains physiological activity of human von Willebrand Factor, comprising:

(a) providing a non-human transgenic mammal having integrated into its genome an exogenous gene construct, wherein said exogenous gene construct comprises:
  (A) 5' expression regulating sequences, including a mammary gland-specific promoter;
  (B) DNA encoding said von Willebrand Factor or fragment thereof, and a signal sequence effective in directing secretion of said von Willebrand Factor or fragment thereof into the milk of said transgenic mammal; and
  (C) 3' regulatory sequences, including a polyadenylation signal, that result in the expression of said DNA encoding said von Willebrand Factor or fragment thereof, in mammary gland cells of said transgenic mammal;
wherein (A), (B) and (C) are operably linked in said exogenous gene construct to obtain production of said von Willebrand Factor or fragment thereof in said mammary gland cells and secretion thereof into the milk of said transgenic mammal;

(b) allowing said DNA encoding von Willebrand Factor or fragment thereof to be expressed and secreted into the milk of said transgenic mammal;

(c) collecting milk from said mammal, and, (d) obtaining von Willebrand Factor or fragment thereof from said milk.

11. The process according to claim 10, wherein said mammal is induced to lactate prior to said collecting step.

12. The process according to claim 10, wherein said promoter is a milk protein gene promoter.

13. The process according to claim 12, wherein said milk protein gene promoter is selected from the group consisting of whey acidic protein, casein, lactalbumin and beta-lactoglobulin promoters.

14. The process according to claim 10, wherein said transgenic mammal produces human von Willebrand Factor.

15. The process according to claim 14, wherein said human von Willebrand Factor has the amino acid sequence of human von Willebrand Factor.

16. The process according to claim 10, wherein said 3' regulatory sequences in said exogenous gene construct are 3' untranslated regions from a milk protein gene or from human von Willebrand Factor.

17. The process according to claim 10, wherein said transgenic mammal is selected from the group consisting of a mouse, rat, rabbit, pig, sheep, goat and cattle.

18. The process according to claim 10, wherein said mammal is a female.

19. The process according to claim 10, wherein said exogenous gene construct comprises a mouse whey acid protein promoter and the 3' regulatory sequence of the mouse whey acid protein gene.

20. A process for producing a non-human transgenic mammal that produces in its mammary gland cells and secretes into its milk a human von Willebrand Factor or fragment thereof which retains physiological activity of human von Willebrand Factor, comprising:

(a) providing an exogenous gene construct, wherein said exogenous gene construct comprises:
  (A) 5' expression regulating sequences, including a mammary gland-specific promoter;
  (B) DNA encoding said von Willebrand Factor or fragment thereof, and a signal sequence effective in directing secretion of said von Willebrand Factor or fragment thereof into the milk of said transgenic mammal; and
  (C) 3' regulatory sequences, including a polyadenylation signal, that result in the expression of said DNA encoding said von Willebrand Factor or fragment thereof, in said mammary gland cells,
wherein (A), (B) and (C) are operably linked in said exogenous gene construct to obtain production of said von Willebrand Factor or fragment thereof in said mammary gland cells and secretion thereof into the milk of said transgenic mammal;

(b) introducing said exogenous gene construct of step (a) into a non-human mammalian embryo, wherein said construct is stably integrated into the genome of said mammalian embryo;

(c) permitting said embryo to develop into a non-human transgenic mammal; and (d) identifying a non-human transgenic mammal that produces said von Willebrand Factor or fragment thereof.

21. The process according to claim 20, wherein said construct of step (a) is in the form of DNA, DNA in a vector, DNA contained in one or more organelles or other parts of a cell or DNA contained in one or more whole cells.

22. The process according to claim 20, wherein said promoter is a milk protein gene promoter.

23. The process according to claim 22, wherein said milk protein gene promoter is selected from the group consisting of whey acidic protein, casein, lactalbumin and beta-lactoglobulin promoters.

24. The process according to claim 20, wherein said transgenic mammal produces human von Willebrand Factor.

25. The process according to claim 24, wherein said human von Willebrand Factor has the amino acid sequence of human von Willebrand Factor.

26. The process according to claim 20 wherein said 3' regulatory sequences in said exogenous gene construct are 3' untranslated regions from a milk protein gene or from human von Willebrand Factor.

27. The process according to claim 20 wherein said transgenic mammal is selected from the group consisting of a mouse, rat, rabbit, pig, sheep, goat and cattle.

28. The process according to claim 20, wherein said mammal is a female.

29. The process according to claim 20, wherein said mammal is a male.

30. The process according to claim 20, wherein said exogenous gene construct comprises the mouse whey acid protein promoter and the 3' regulatory sequence of the mouse whey acid protein gene.

31. Cells obtained from the non-human transgenic mammal of claim 1, wherein said cells contain said exogenous gene construct which is stably integrated into the genome of said cells.

32. The cells according to claim 31, wherein said cells produce said von Willebrand Factor or fragment thereof.

* * * * *